US012788865B2

(12) United States Patent
Hickmott et al.

(10) Patent No.: US 12,788,865 B2
(45) Date of Patent: Nov. 10, 2026

(54) IRRIGATION SYSTEM

(71) Applicant: Coloplast A/S

(72) Inventors: Richard Morgan Hickmott, Helsingoer (DK); Aaron Wansch, Malmoe (SE)

(73) Assignee: Coloplast A/S, Humlebaek (DK)

( * ) Notice: Subject to any disclaimer, the term of this patent is extended or adjusted under 35 U.S.C. 154(b) by 983 days.

(21) Appl. No.: 18/014,186

(22) PCT Filed: Jul. 2, 2021

(86) PCT No.: PCT/DK2021/050224
§ 371 (c)(1),
(2) Date: Jan. 3, 2023

(87) PCT Pub. No.: WO2022/002340
PCT Pub. Date: Jan. 6, 2022

(65) Prior Publication Data

US 2023/0277755 A1 Sep. 7, 2023

(30) Foreign Application Priority Data

Jul. 3, 2020 (DK) .......................... PA 2020 70457
Dec. 4, 2020 (DK) .......................... PA 2020 70812

(51) Int. Cl.
*A61M 3/02* (2006.01)

(52) U.S. Cl.
CPC ........ *A61M 3/0237* (2013.01); *A61M 3/0245* (2013.01); *A61M 3/0254* (2013.01); *A61M 3/0266* (2013.01); *A61M 2202/068* (2013.01); *A61M 2205/07* (2013.01)

(58) Field of Classification Search
CPC .............. A61M 3/0258; A61M 3/0262; A61M 3/0233; A61M 3/0237
See application file for complete search history.

(56) References Cited

U.S. PATENT DOCUMENTS

| | | | | |
|---|---|---|---|---|
| 5,807,320 A | 9/1998 | Kammerer | | |
| 6,669,668 B1 | 12/2003 | Kleeman et al. | | |
| 8,157,782 B2 * | 4/2012 | Marak | A61M 5/148 | 604/408 |
| 10,398,811 B1 * | 9/2019 | Nguyen | A61M 3/022 | |
| 2003/0114834 A1 * | 6/2003 | Mezzoli | A61M 3/027 | 604/540 |

(Continued)

FOREIGN PATENT DOCUMENTS

| | | | |
|---|---|---|---|
| CN | 103127570 A | 6/2013 | |
| ES | 2627829 A1 | 7/2017 | |

(Continued)

*Primary Examiner* — Courtney Fredrickson
(74) *Attorney, Agent, or Firm* — Coloplast Corp., Coloplast A/S; Nick Baumann

(57) ABSTRACT

An anal irrigation system with a box for a reservoir is provided. The reservoir may be for one-time use and disposed of after use. The box is provided with means for pressing so that the box can be used to displace liquid from a reservoir in an easy and convenient way. Also provided is a box with means for pressing so as to displace liquid from a reservoir. Also provided is an anal irrigation system without reservoir and where the box is provided with an inflatable lung, which is inflated for displacing the liquid from the box.

10 Claims, 10 Drawing Sheets

(56) References Cited

U.S. PATENT DOCUMENTS

| | | | | |
|---|---|---|---|---|
| 2006/0025728 | A1* | 2/2006 | Leiboff .............. | A61M 3/0287 604/317 |
| 2011/0306941 | A1* | 12/2011 | Chandrasekar ..... | A61M 3/0254 604/262 |
| 2014/0100518 | A1 | 4/2014 | Baxter et al. | |
| 2017/0274143 | A1* | 9/2017 | Sanchez, Jr. ............ | A61F 9/007 |
| 2018/0369457 | A1 | 12/2018 | Borgmeier et al. | |
| 2020/0206411 | A1 | 7/2020 | Henry et al. | |

FOREIGN PATENT DOCUMENTS

| | | | |
|---|---|---|---|
| WO | 2010115431 | A2 | 10/2010 |
| WO | 2018188710 | A1 | 10/2018 |

* cited by examiner

IRRIGATION SYSTEM

The invention relates to a system for anal irrigation and a box for use in a system for anal irrigation.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 6A illustrates the system prior to use and FIG. 6B illustrates the system during use.

FIG. 7A illustrates the system prior to use and FIG. 6B illustrates the system during use.

FIG. 8A illustrates the system prior to use and FIG. 8B illustrates the system during use.

FIG. 9A illustrates a top view of the box with an open lid and FIG. 9B illustrates a cross-sectional view with the box with a closed lid.

FIGS. 25-26 illustrate top views and FIG. 27 illustrate a cross-sectional view.

DETAILED DESCRIPTION

Figure 1:
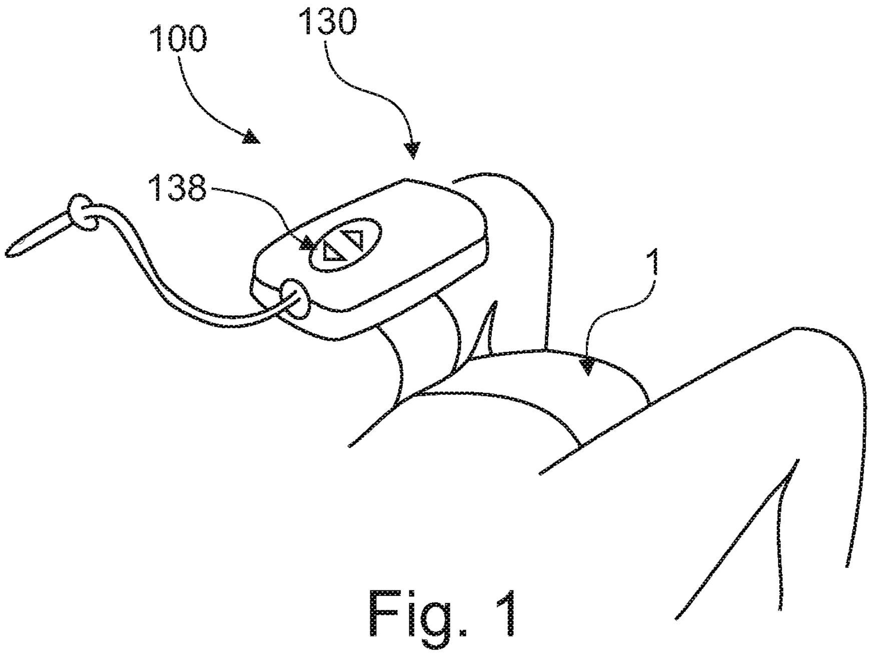
FIG. 1 illustrates an anal irrigation system positioned on a thigh of a user and ready for use.

Trans-anal irrigation, or rectal irrigation, is referred to as anal irrigation and provides a process for emptying the lower bowel of faecal matter. Anal irrigation benefits people who suffer from neurological disorders associated with a spinal injury, *spina bifida*, multiple sclerosis, Parkinson's disease, or other neurological diseases; sensory disorders that might arise after surgery to treat colitis; or issues of tissue elasticity associated with aging. People who benefit from anal irrigation often have limited dexterity.

Embodiments described below provide an anal irrigation system (AIS) having a disposable component and a reusable component. The disposable component includes in some embodiments a reservoir to hold an amount of liquid, a probe for insertion into the rectum, and a tube connected between the reservoir and the probe. In other embodiments, the disposable component includes a reservoir to hold an amount of liquid, the reservoir being connectable to a reusable tube, which in turn is connectable to a disposable probe. The reusable component provides a box or a container that receives the reservoir of the disposable component, where the box is adapted to compress the reservoir to displace the liquid from the reservoir and out of the probe.

The advantages of the AIS include a compact box that can be easily handled by the user, where the box is simple in form and is not pressurized. The box provides a variety of mechanical approaches for reducing a space inside of the box, which proportionally collapses the walls of the reservoir to displace a proportional amount of liquid out of the reservoir and through the anal probe. The box generally has smooth, clean exterior walls that allow the user to easily handle the box. The internals of the box move or otherwise displace to reduce an effective inside volume of the box. The reduced internal volume of the box results in the reservoir being squeezed to displace the liquid in the reservoir.

During use, the reservoir is inserted into the box with the tube and anal probe projecting out of the box. The user initiates a compression of the reservoir, where for example, the effective internal space of the box is reduced (by walls coming together or by a roller motion), which pushes the liquid out of the reservoir and through the anal probe. The reservoir, tube, and probe are in some embodiments discarded upon completion of the anal irrigation. In other embodiments, the tube may be reused, and the reservoir and probe are discarded upon completion of the anal irrigation. The box is not pressurized, or in other words, the box is not a pressure vessel. Thus, the liquid flowing from the probe can be selectively and willfully stopped by the user without moving valves or depressurization of the system pressure. The user has direct and better control and receive the amount of irrigation they desire. There is no need to clean the reservoir or probe between uses as they are discarded.

Embodiments relate to an anal irrigation system comprising:

- an anal probe, a reservoir configured to contain irrigation liquid and tubes connecting the reservoir with the anal probe, the reservoir having flexible wall portions and
- a box having a shell that forms an exterior surface of the box and defines an interior space within the box, and the interior space of the box includes a reservoir holding cavity,
- the box having means for pressing on an exterior surface of the reservoir thereby displacing the irrigation liquid from the reservoir.

Embodiments relate to an anal irrigation system comprising:

- a box having a shell that forms an exterior surface of the box and defines an interior space within the box, and the interior space of the box includes a reservoir holding cavity;

- a tube connected between an anal probe and a reservoir, the reservoir is sized for placement in the reservoir holding cavity and configured to contain irrigation liquid; and
- wherein the box comprises a movable element located in the interior space, and the movable element is configured to move relative to the reservoir holding cavity to compress the reservoir and displace the irrigation liquid from the reservoir.

Embodiments relate to an anal irrigation system comprising:

- a tube connected between an anal probe and a reservoir, with the reservoir configured to contain irrigation liquid; and
- a non-pressurized box defining a cavity comprising a plate, with the cavity sized to receive the reservoir;
- wherein, when the reservoir is placed in the cavity, movement of the plate compresses the reservoir and displaces irrigation liquid through the tube and out of the anal probe.

Embodiments relate to an anal irrigation system comprising:

- a tube connected between an anal probe and a reservoir, with the reservoir configured to contain irrigation liquid;
- a box defining a cavity comprising a plate, with the cavity sized to receive the reservoir; and
- means for displacing the plate to reduce an effective volume of the cavity.

Embodiments relate to a box having a shell that forms an exterior surface of the box and defines an interior space within the box, and the interior space of the box includes a reservoir holding cavity; the box being configured for use in an anal irrigation system, wherein the box is configured to hold a reservoir with a volume of anal irrigation liquid, the box including means for pressing on an exterior surface of the reservoir to displace the anal irrigation liquid from the reservoir.

Embodiments relate to an anal irrigation system comprising

- an anal probe, a reservoir configured for containing irrigation liquid and tubes connecting the reservoir with the anal probe, the reservoir having flexible wall portions and
- a box configured for holding the reservoir during an irrigation cycle,
- the box having pressure inducing means in the form of an air pump configured for inducing pressure on an exterior surface portion of the reservoir thereby displacing liquid from the reservoir.

Embodiments relate to an anal irrigation system comprising

- an anal probe, tubes connected to or connectable to the anal probe and
- a box having a shell that forms an exterior surface of the box and defines an interior space within the box, the interior space being configured for holding liquid during an irrigation cycle,
- the box being provided with an inflatable lung, which is configured for being inflated during use and thereby displacing the liquid from the reservoir.

Users of anal irrigation systems typically have poor hand dexterity. Therefore, simple systems requiring little, or no setup are advantageous for the users. Systems as described in this disclosure are very simple to set up prior to use and requires no, or almost no connections to be made prior to use.

The box as disclosed herein provides an easy and convenient way for displacing irrigation liquid from a reservoir. This is an advantage, in particular for users with poor hand dexterity, who might find it difficult to use an irrigation system.

In the context of this disclosure the proximal end of the anal probe, the tube and so forth is the end closest to the user in use and the distal end is the opposite end.

The anal probe may be in the form of a through-going tubular element with an interior lumen configured for allowing flow of irrigation liquid. The anal probe will typically include retention means. The outer diameter of such an anal probe is typically about 8-16 mm, for example 10 mm. The length is about 70-200 mm, for example about 150 mm.

The box described in this disclosure may be made of rigid material such as Acrylonitrile butadiene styrene (ABS), Polycarbonate (PC), combinations of PC and ABS, acrylic (PMMA), Polypropylene PP or other types of plastic material.

The box includes any of several means for pressing as further described below. The material of the box has a rigidity such that it is able to withstand the pressure from the means for pressing and to provide a backstop for the pressure. However, the box is not a pressure vessel and need not be pressurised to deliver irrigation liquid to the probe, i.e., the box is not gas-tightly sealed.

In case no reservoir is used, the box is liquid tight. This means that the box is provided with sealings at any opening into the box. As mentioned above, any provision of sealing is not configured for providing a gas-tight seal.

In the context of this disclosure, the means for pressing configured for displacing liquid means that the liquid is displaced directly by the means and without pressure being built-up in the box. The anal irrigation system including the box does not rely upon valves or stops to meter or contain an increased pressure in the box for release at a later stage. Contrary to this, the system is configured to have a direct link between the pressing by the means for pressing and the displacement of liquid. In other words, the means for pressing are configured to displace the liquid by direct interaction between the means for pressing and the reservoir, in such a way that activation of the means for pressing leads to liquid being displaced.

The reservoir is made of flexible material or at least comprising flexible wall portions configured for be compressed by the means for pressing. Examples of material are Polyethylene, Polyvinylchloride or Thermoplastic elastomeric material. Environmentally friendly material such as corn starch may also be used. The reservoir may be made of a very thin-walled material with a thickness of less than 100 μm or even in the range of 10 to 50 μm. The reservoir is configured for containing approximately 1 litre of irrigation liquid but may be larger or smaller, if preferred. The irrigation liquid may be tap water but may also include a saline solution.

Embodiments relate to the means for pressing to be a roller configured for curling up the reservoir. The roller may include a slot so that the reservoir is inserted into the slot, caught here and curled up around the roller to thereby displace the liquid from the reservoir. In these embodiments, the box may have a scraper on a sidewall behind the roller, so as to assist in pushing out the liquid from the reservoir.

Embodiments relate to means for pressing in the form of an actuator in combination with a pressure plate. The linear actuator may be electrically driven so that the user can manipulate it by simply pressing a button on the box.

By using a pressure plate, it is possible to easily and with certainty check how far the pressure plate is moved. This provides an accurate reading of how much the volume of reservoir has been decreased and thereby how much liquid has been irrigated through the system and thus instilled into the bowels of the user.

The actuator may be positioned at a sidewall of the box and be configured for pushing the pressure plate towards an opposite sidewall. In these cases, the actuator is a linear actuator.

The pressure plate may be connected by a hinge to a sidewall of the box and configured for being tilted. In these cases, the actuator may be rotatable or linear or both.

Embodiments relate to the means for pressing to be in the form of an inflatable lung.

The inflatable lung may be inflated by an air pump. The air pump may be electrically or manually driven. The inflatable lung may be subdivided into chambers, such as two, three, four or five chambers. The subdivision will allow the user to detect how much liquid has been irrigated into the bowels, because each chamber may be able to displace a certain amount of liquid from the reservoir.

Embodiments relate to the box including a lid.

Embodiments relate to the lid including the means for pressing.

Embodiments relate to the anal probe being firmly and not detachably connected to the tube, which in turn is firmly and not detachably connected to the reservoir.

This provides for a very simple and reliable system. Prior to use, the user fills liquid into the reservoir and inserts the reservoir into the box and then the system is ready to use. No further preparation or connection of the system is needed. Following use, the user simply removes the reservoir including the tube and anal probe from the box and disposes these single-use components. No disconnection of tubes, cleaning of tubes and so forth is required. Furthermore, because the system is connected when the user receives it, such a system removes any possibility of user-induced faulty connections which might lead to misuse of the system.

Embodiments relate to the anal probe including a foam element on an exterior surface of the tubular element of the anal probe, which foam element is configured for retaining the anal probe in the rectum during the irrigation procedure. The foam element may be in the form of a cuff.

Embodiments relate to the anal probe including an inflatable balloon.

In these embodiments, the box may include a second line for pumping air into the inflatable balloon or a second chamber.

Embodiments relate to the box comprising holding means configured for holding the box in place at the upper side of the thighs of a user. The holding means may be configured for holding the box in place at an upper side of one thigh or may alternatively be configures for holding the box in place at an upper side of both thighs.

Embodiments relate to the box comprising a strap configured for holding the box in place at a thigh of a user. The strap may be made of a suitable fabric and comprise hooks and loops for closing it. As an example, the strap may be made of polychloroprene.

Embodiments relate to the anal irrigation system or the box comprising a pair of foldable arms, which are configured for holding the box in place at a thigh of a user.

The distance between the arms may be adapted for allowing positioning over one thigh or may alternatively be adapted for allowing positioning over both thighs of a user.

The arms may be made of the same material as the box and may extend 20-25 cm downwards from a lower side of the box in an unfolded configuration. Transverse to the folding direction, the arms may be 10 cm wide. To allow for the folding/un-folding of the arms, they may each be provided with a hinge extending transversely across the arm in a distance of 2-5 cm from the lower side of the box. The hinge may be a living hinge or a friction hinge. The distance between the arms may be 10-20 cm, or larger depending on whether the distance is adapted for fitting the arms over one thigh or both thighs. In case, the arms are adapted for fitting over both thighs, the distance between them may be 30 cm or more. The arms may also be configured for being folded outwards (180 degrees) so as to provide a larger base for the box. In this way, the box with the completely unfolded arms may be positioned across both thighs.

Alternatively, the arms may be configured for being positioned in a variety of positions. The arms may have a multitude of hinged sections so that they are malleable in various positions.

Embodiments relate to the reservoir being provided with first coupling means and the box being provided with second coupling means, wherein the first coupling means are configured for cooperating with the second coupling means so as to provide a coupling for filling the reservoir when it is situated in the box.

Such embodiments are advantageous in case the reservoir is thin-walled and very flexible. A thin-walled and very flexible reservoir will be somewhat flimsy in structure and may therefore be difficult to control during filling and subsequent insertion into the box. Therefore, it may be an advantage to couple the reservoir to the box prior to filling and then fill the reservoir through the box. For that purpose, the box is provided with a filling opening positioned at the coupling.

Embodiments relate to the first coupling means being 50-100 mm in diameter. The second coupling means may also be 50-100 mm in diameter. In embodiments the first coupling means comprise a c-shaped channel configured for cooperating with a ridge on the second coupling means so as to provide a coupling between the first and second coupling means. In embodiments, the first coupling means comprise a first upstanding ridge, which is configured for cooperating with a second upstanding ridge on the second coupling means, such that the first upstanding ridge circumferentially surrounds the second upstanding ridge. The first upstanding ridge may in this embodiment be rolled over the second upstanding ridge for coupling the two coupling means together.

Embodiments relate to the box having a closure for closing the filling opening. The closure may be hinged to a top wall of the box.

Embodiments relate to the tubes being connected to the box through a connector on the tube configured for cooperating with a through-going opening at the box. These embodiments are particularly useful, if the anal irrigation system has no reservoir, because the box in this case is closed and liquid tight. However, connection of the tubes to the box may also be done in embodiments provided with a reservoir.

The connector may as examples be a luer-lock type of connector, a threaded connector or a bayonet connector.

DETAILED DESCRIPTION OF THE DRAWING

Embodiments, and features of the various exemplary embodiments described in this application, may be combined with each other ("mixed and matched"), unless specifically noted otherwise.

Figure 2:
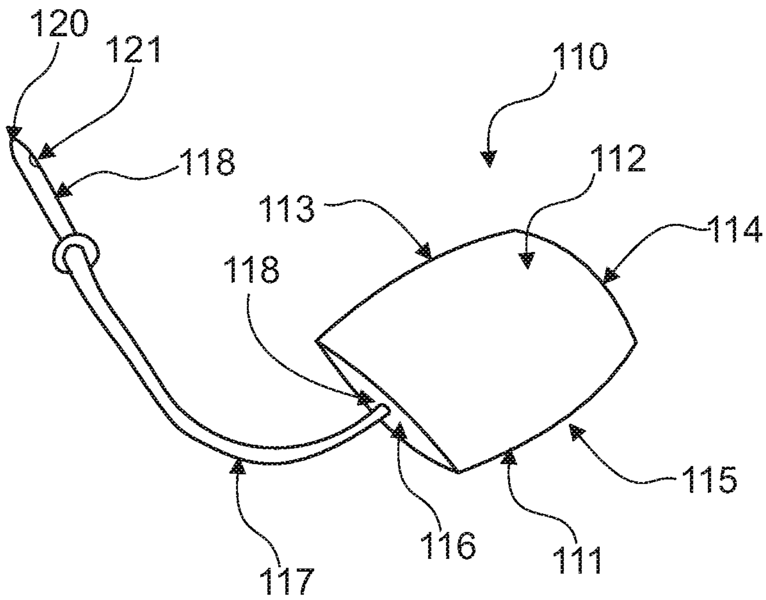
FIG. 2 illustrates a reservoir, tube and anal probe in one disposable element.

FIGS. 1 and 2 illustrate sketches of an irrigation system 100 as disclosed herein. The irrigation system 100 is in FIG. 1 shown in a ready-to-use state positioned on a user who is sitting on a toilet-seat 1 (only partly shown). The system comprises a box 130 configured for holding a reservoir 110 (FIG. 2). The reservoir 110 in the illustrated embodiment is configured for containing approximately 1 litre of irrigation liquid, but may be larger or smaller, if desired. The box 130 is made of rigid material as described above. The box 130 provides a container for the reservoir 110, and as such, the box is not pressurized or sealed against an escape of liquid or air. The box may be provided with actuating buttons 138 on a top surface thereof. The box may also include feedback indicators 139 in the form of an array of LEDs. The feedback indicators 139 may indicate the amount of liquid emptied from the reservoir such that for example 5 indicators are used, and one light up when ⅕ has been emptied, the next light up when a further ⅕ has been emptied and so forth. The feedback may be obtained as explained below in relation to specific embodiments.

FIG. 2 illustrates an embodiment of a reservoir 110, where the reservoir comprises two walls 111, 112, welded along three edges 113, 114, 115, each wall 111, 112 formed of a foil material. At the fourth edge, the reservoir comprises a proximal foil 116 inserted between the walls 111, 112. A tube 117 is attached to the top foil 116. In the illustrated embodiment, the tube 117 is firmly attached to the top foil, e.g., by welding the parts together such as shown at 118. The tube 117 may also be connected to a connector welded to the top foil, such as a snap-fit or bayonet connector. During use, the interior lumen of the reservoir is in fluid communication with an interior lumen of the tube, so that the irrigation liquid can flow from the reservoir and through the tube to an anal probe 119. In a proximal end of the tube, an anal probe is attached. In the illustrated embodiment, the anal probe 119 is firmly attached to the tube, but it may also be connected using a connector, e.g., a snap-fit or bayonet connector. In the illustrated embodiment the anal probe is shown with a closed tip 120 and an eyelet 121 through which irrigation liquid may exit during use. However, other configurations such as an open tip may also be used. The anal probe 118 may be provided with retention means (not shown) in the form of a foam cuff or an inflatable balloon.

Figure 3:
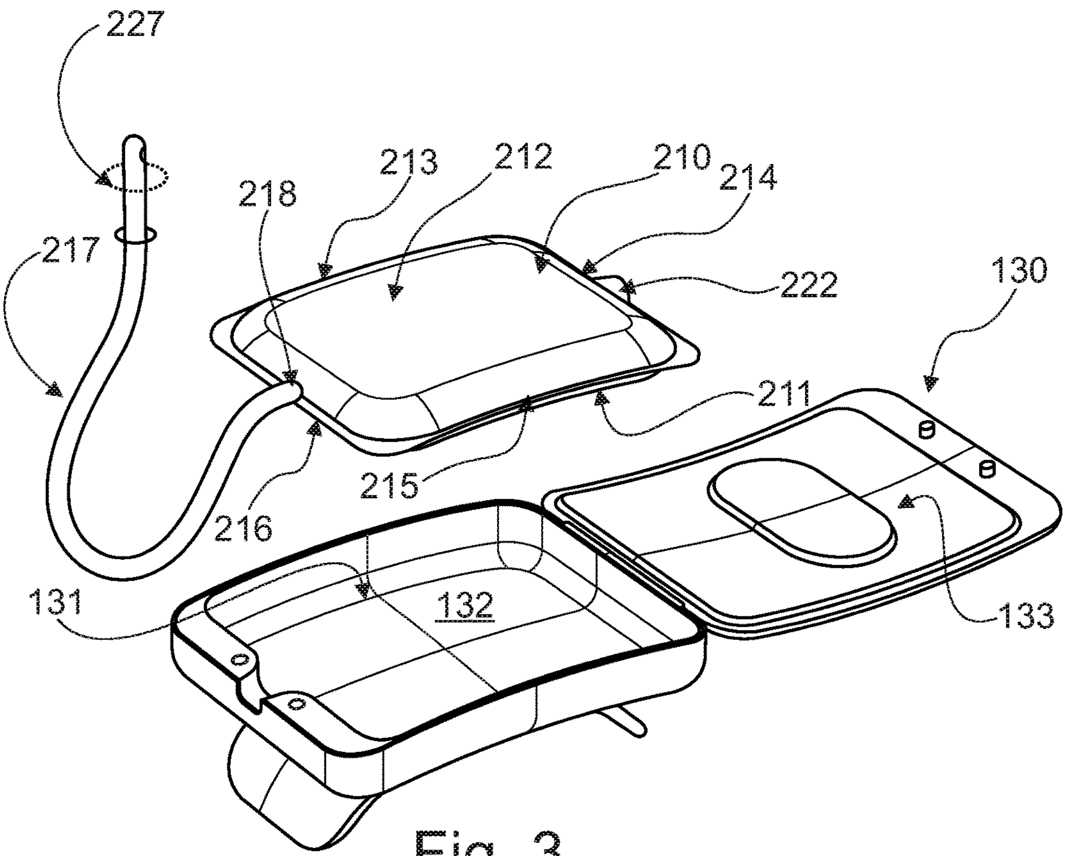
FIG. 3 illustrates a perspective view of an anal irrigation system with a reservoir, tube and anal probe and a box including means for pressing.
Figure 4:
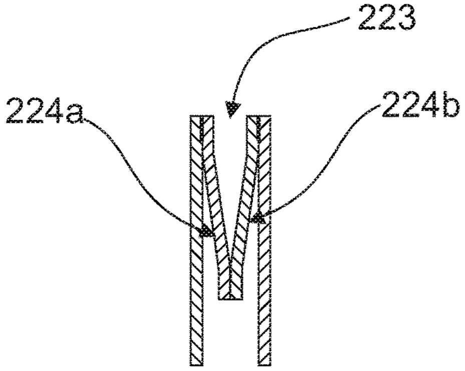
FIG. 4 illustrates a one-way foil valve suitable to be used in a reservoir.

FIG. 3 illustrates how the reservoir is configured to be held in the box 130. The reservoir 210 illustrated in FIG. 3 has walls 211, 212 which are welded along all four edges, 213, 214, 215, 216. At one weld, a filling spout 222 is provided. The tube 217 is welded to the reservoir in one of the welds as indicated at 218. The filling spout 222 may be in the form of one-way valve, with valve foils 224*a*, 224*b* inserted in the opening 223 as indicated in FIG. 4.

Figure 5:
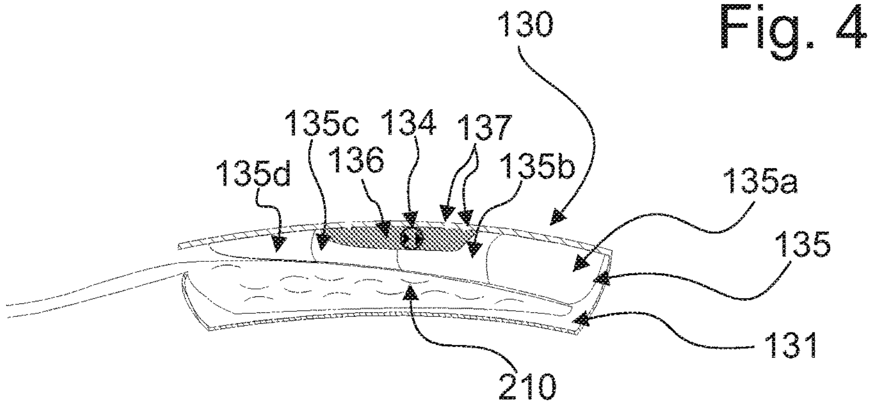
FIG. 5 illustrates a cross-sectional view of an anal irrigation system with a reservoir inserted into a cavity of a box and where the reservoir is subjected to press from means for pressing in the box.

The box 130 has a cavity 131, which is configured for holding the reservoir 210 during the irrigation procedure. In the illustrated embodiment, the box 130 is made of rigid material and it is an advantage if the floor or lower interior wall 132 of the cavity is rigid. The floor 132 is the lowermost part of the cavity, when the box sits on the leg of a user. The floor 132 should be suitable for providing a back-stop for means for pressing 133 in the box. The means for pressing 133 is in the illustrated embodiment in the form of a pump 134 (see FIG. 5) and an inflatable lung 135, which is best seen in the cross-sectional view in FIG. 5. The inflatable lung may be subdivided into a number of chambers 135*a*, 135*b*, 135*c*, 135*d*, which allows for a feedback to the user of how big a portion of the reservoir has been subjected to pressure—and thereby how much liquid has left the reservoir. The box 130 includes a second cavity 136 in the lid, which is configured for holding the pump 134 and connections to the pump (not shown) from actuating buttons on a top surface—see FIG. 1. The pump may be provided with air-inlets 137 leading air into the second cavity 136.

Figure 6A:
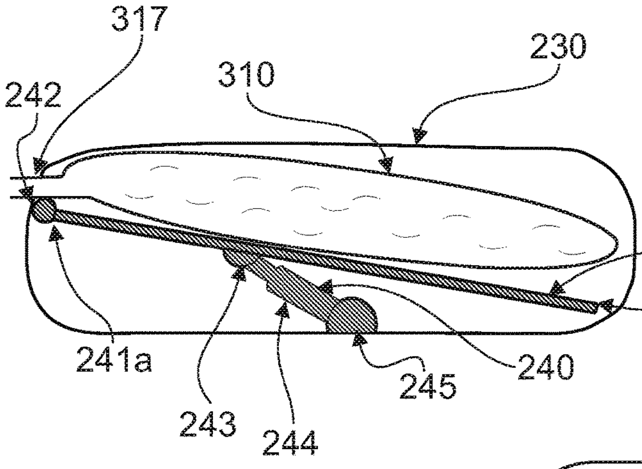
FIGS. 6A, 6B illustrate cross-sectional views of an anal irrigation system with a reservoir inserted into a cavity of a box.
Figure 6B:
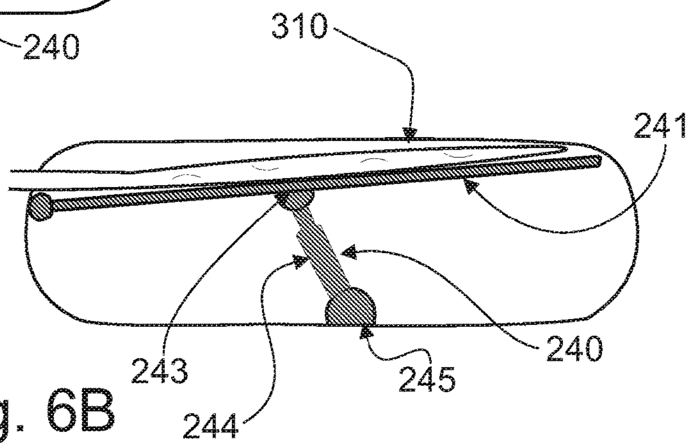

FIGS. 6A, 6B illustrate a box 230 and a reservoir 310 inserted into the box 230, where the means for pressing are in the form of an actuator 240 positioned under a tiltable pressure plate 241. The pressure plate 241 is tiltable around a setting 242, which provides for a hinged attachment of the pressure plate 241 to an interior side wall of the box 230. The pressure plate thus extends from a first end 241*a* attached to the setting 242 to a second end 241*b* which is freely movable up and down. The actuator 240 comprises a ball-shaped connection 245 at the lower side of the box, a linear actuator part 244, which is telescopically extendable and a support 243 for supporting the pressure plate 241. In a first position, as shown in FIG. 6A, the linear actuator part 244 is extended so that the support 243 is positioned closer to the first end 241*a* at the setting 242 than to the second end 241*b* of the floor.

In FIG. 6B, the pressure plate 241 is tilted around the setting 242. The actuator is in a more upright position with respect to the lower side of the box, such that linear actuator 244 is slightly shorter due to having been telescopically collapsed slightly as compared to FIG. 6A. At the same time, the actuator is rotated at the rotatable ball-shaped connection 245. This means that the support 243 has moved sideways toward the middle portion of the floor 241 and thus the pressure plate tilts from the upper right corner of the box downwards towards the setting 242. Thus, little room is left for the reservoir, which has then been squeezed. As a result, the liquid has been displaced from the reservoir through the tube 317 and out the anal probe (not shown). The position of the actuator can provide a feedback to the user of how much pressure has been put on the reservoir and thereby how much liquid has left the reservoir.

Figure 11:
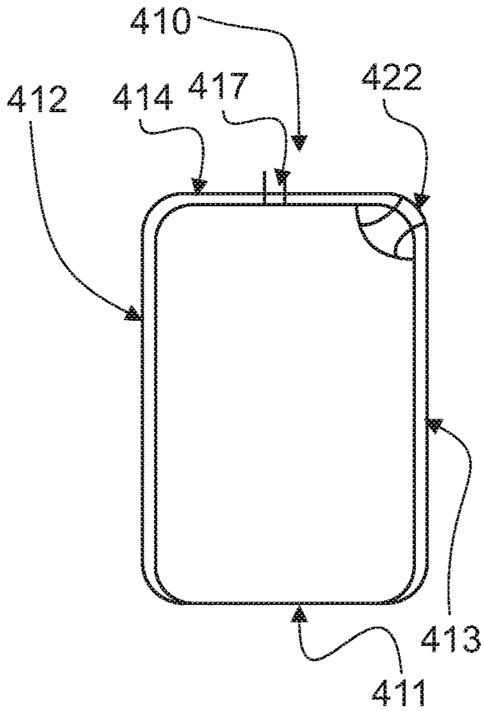
FIGS. 11 and 12 illustrate reservoirs.

The reservoir 310 is illustrated in FIG. 11 as a folded foil, which is closed and welded at three sides 312, 313, 314 and folded at the fourth side 311. The tube 317 is welded to the top 313 of the reservoir e.g. by inserting the tube between the foils and welding around it. (. At the top, there is also a filling spout 322. The filling spout 322 is conveniently located at one corner of the reservoir and may be formed with a foil-valve as illustrated in FIG. 4.

Figure 7A:
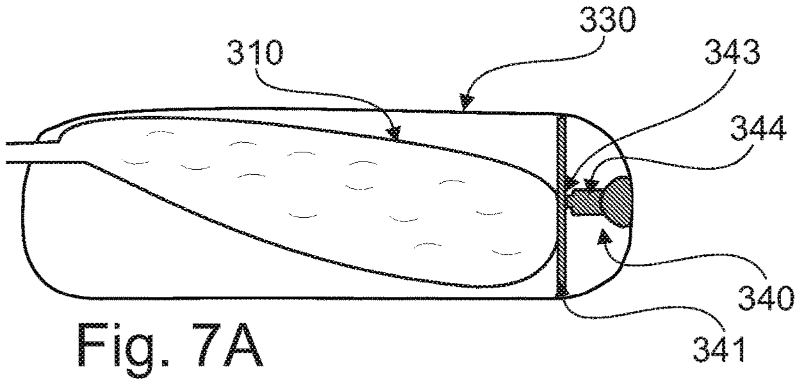
FIGS. 7A, 7B illustrate cross-sectional views of an anal irrigation system with a reservoir inserted into a cavity of a box.
Figure 7B:
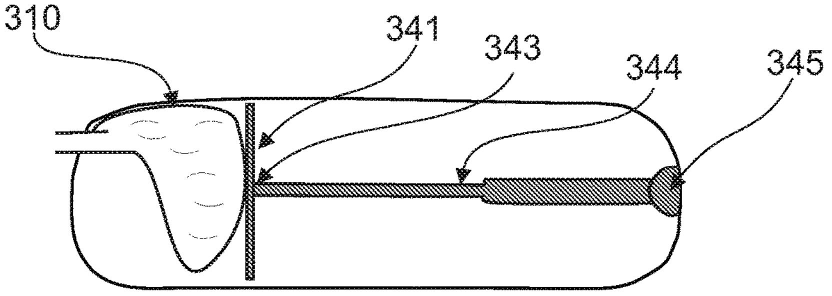

FIGS. 7A, 7B illustrate a box 330 including a reservoir 310; the reservoir 310 is in this embodiment the same as in the embodiment of FIGS. 6A, 6B. The box 330 comprises a linear actuator 340 and a pressure plate 341. The linear actuator 340 includes an actuator rod 344 which is attached to a sidewall of the box at a connection 345 and to the pressure plate at a connection 343. In FIG. 7A, the pressure plate 341 is at its rest position and the reservoir is still filled with irrigation liquid. The linear actuator 340 is also in its rest position with actuator rod 344 completely collapsed. In FIG. 7B, the pressure plate 341 is at a position closer to the opposite sidewall and the reservoir is nearly emptied. The linear actuator 340 is at an extended position with the actuator rod 344 telescopically extended compared to FIG. 7A. The extension of the actuator rod will allow for providing a feedback to user about how much pressure has been put on the reservoir and thereby how much liquid has left it.

Figure 8A:
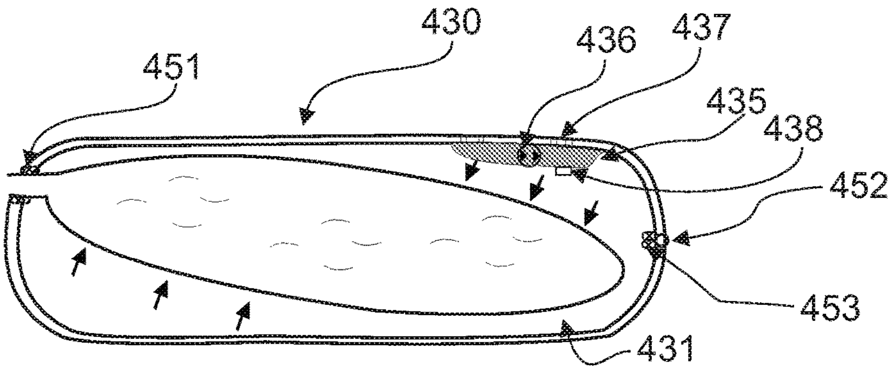
FIGS. 8A, 8B illustrate cross-sectional views of an anal irrigation system with a reservoir inserted into a cavity of a box.
Figure 8B:
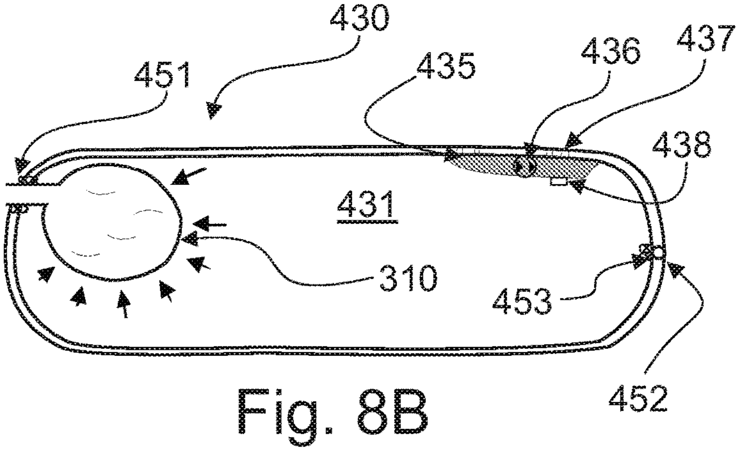

FIGS. 8A, 8B illustrate a box 430 having a pump 450 for increasing the pressure inside the box. The box 430 is sealed 451 at the tube connection, and also sealed 452 at the hinge 453 oppositely positioned to the tube connection. Furthermore, there are seals at the edges (not shown) thus providing an air-tight first cavity 431. When the pump 450 pumps air into the interior of the box, the pressure inside the box will increase and thus displace the liquid from the reservoir—indicated by the arrows. The pump 450 is fed air through the inlets 437 at a top of the box. The inlets may conveniently be provided with one-way valves so as to prevent air from leaving through these inlets. The pump 450 is located in a second cavity 436 at a top of the box. Air is fed from the pump through a connection 438 into the larger first cavity 431, which includes the reservoir 310. The amount of air pumped into the cavity 431 allow for a feedback to the user on how much pressure has been put on the reservoir and thereby how much liquid has left it.

Figure 9A:
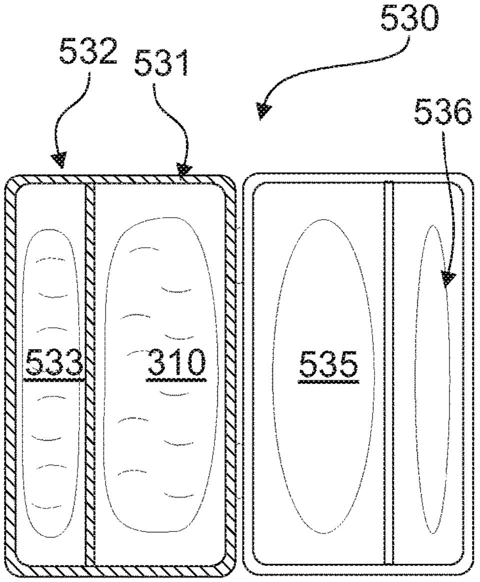
FIGS. 9A, 9B illustrate a top view and a cross-sectional view of an anal irrigation system including a box with two chambers.
Figure 9B:
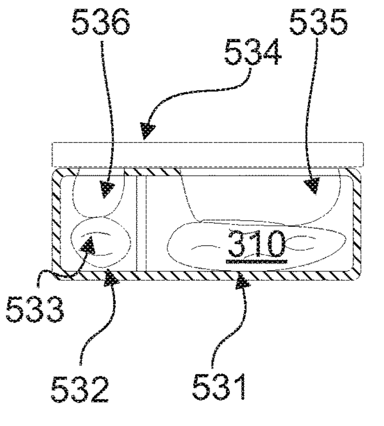

FIGS. 9A and 9B illustrate a box 530, which has two chambers 531, 532 inside it. The larger chamber 531 is configured for holding the reservoir bag as described in the embodiments above. The smaller chamber 532 is configured for holding a smaller reservoir 533 of liquid, which is used to inflate an inflatable balloon on an anal probe (see FIG. 3). The lid of the box 534 has two inflatable lungs, a larger lung 535 configured for functioning as means for pressing on the reservoir for irrigation liquid and a smaller lung 536 configured for functioning as means for pressing on the smaller reservoir for inflating the balloon. A common pump (not shown) may be used to selectively inflate both lungs 535, 536 and may be electrically or manually driven. There may be a simple switch switching between pumping of the air between the two lungs.

Figure 10:
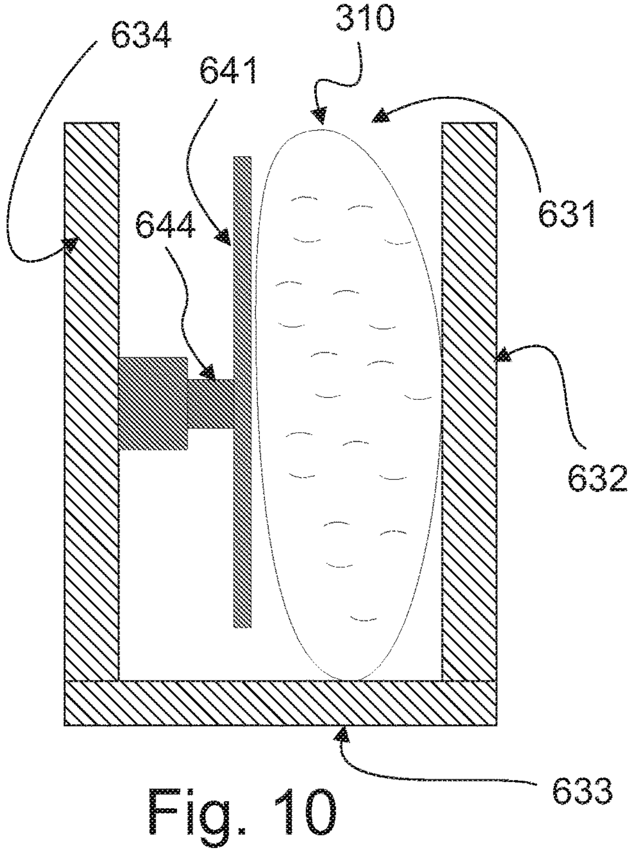
FIG. 10 illustrates a cross-sectional views of an anal irrigation system with a reservoir inserted into a cavity of a box.

FIG. 10 illustrate a box 630, which is upstanding as compared to the embodiments illustrated in FIGS. 6, 7, 8 and 9. This means that the sidewalls 632, 634 are larger than the bottom wall 633. In the illustrated embodiment, a linear actuator 640 as illustrated in connection with FIGS. 7A, 7B, is used as means for pressing. The linear actuator has an actuator rod 644, which is shown half-way extended. The reservoir 310 is shown as halfway empty and being subjected to pressure from the pressure plate 641. This embodiment has the advantage that no lid is required. The gravity on the reservoir 310 will ensure that this is kept inside the cavity 635 of the box.

Figure 12:
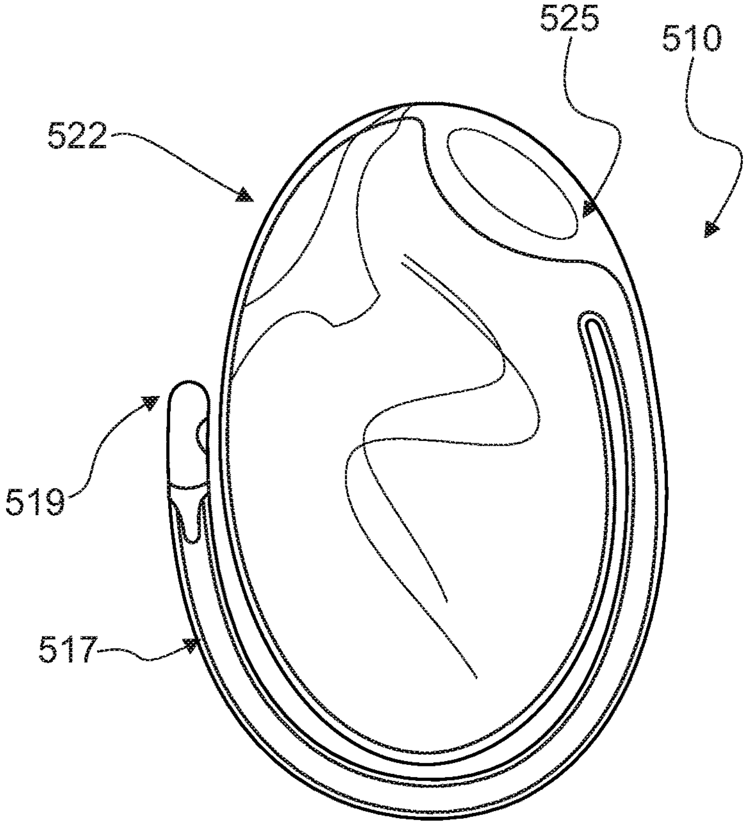

FIG. 12 illustrates a reservoir 510, tube 517, catheter 519 all in one, which is made in a compact way. The reservoir 510 is generally elliptically shaped, and the tube 517 is cut as notch going approximately halfway around the ellipse. At a proximal end of the tube, an anal probe 519 is firmly attached. Furthermore, there may be a filling spout 522 in one end and a handle 525 conveniently positioned on the reservoir.

Figure 13:
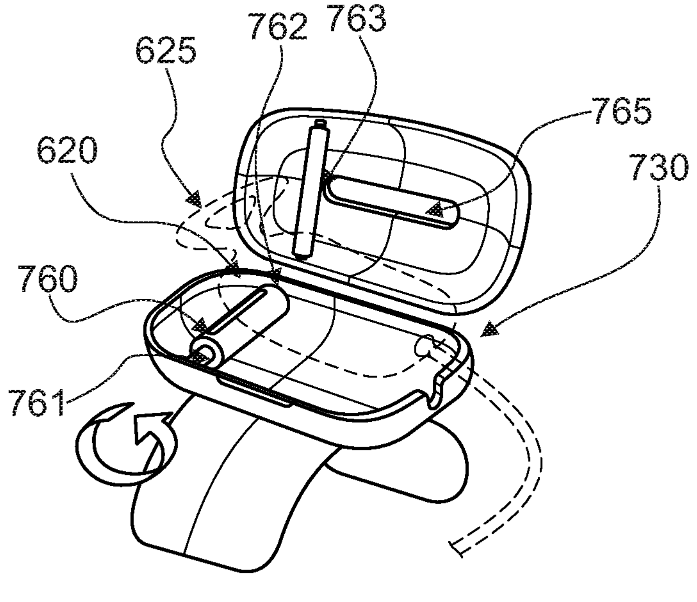
FIGS. 13 and 14 illustrate perspective views of an anal irrigation system with roller functioning as means for pressing.
Figure 14:
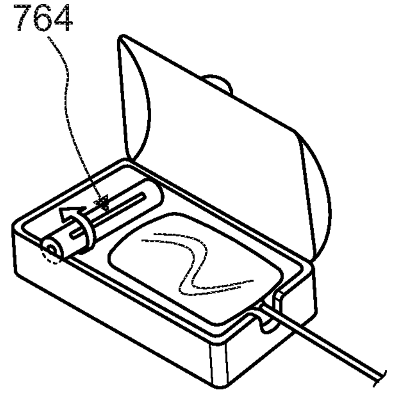

FIGS. 13 and 14 illustrate an anal irrigation system, where the box 730 includes means for pressing in the form of a roller 760. The roller is attached to sidewalls of the box at 761 and opposite to that at 762 so that the roller can roll inside the box. The box may further include a catch 763 for cooperating with the roller to catch the reservoir 620 between them. The reservoir 620 is provided with handles 625, which may be held during filling of the reservoir. An opening (not shown) into the reservoir may be positioned between the handles. The only difference between FIGS. 13 and 14 is that instead of using a catch as in FIG. 13, the roller is provided with a slot 764 through which the reservoir can be inserted and caught prior to curling up around the roller. The box may be provided with a window 765 in a lid, so that the user can see how much of the reservoir bag has been curled up around the roller.

Figure 15:
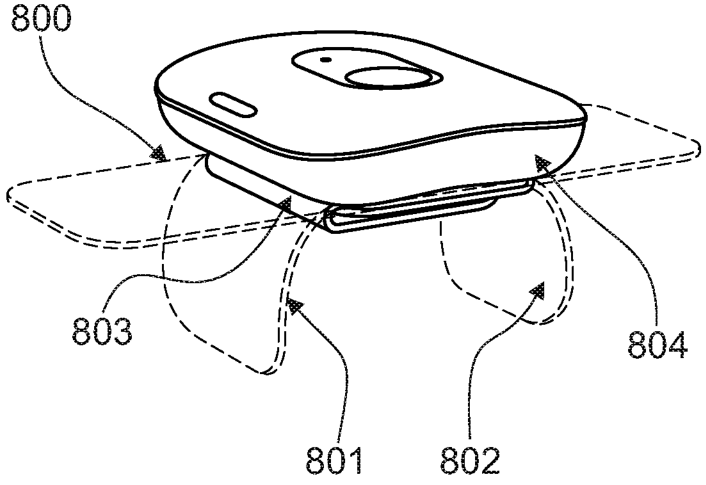
FIGS. 15 to 17 illustrate a box with foldable arms and how it can be positioned during use.
Figure 16:
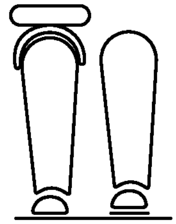
Figure 17:
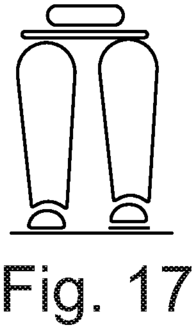
Figure 18:
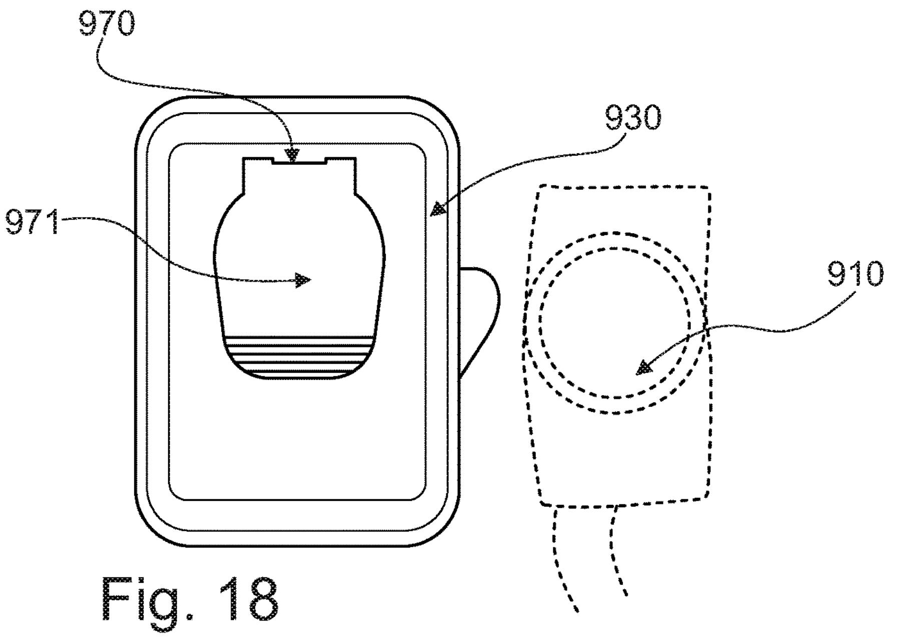
FIGS. 18 to 23 illustrate steps of preparing a box and a reservoir for use in an anal irrigation system.
Figure 19:
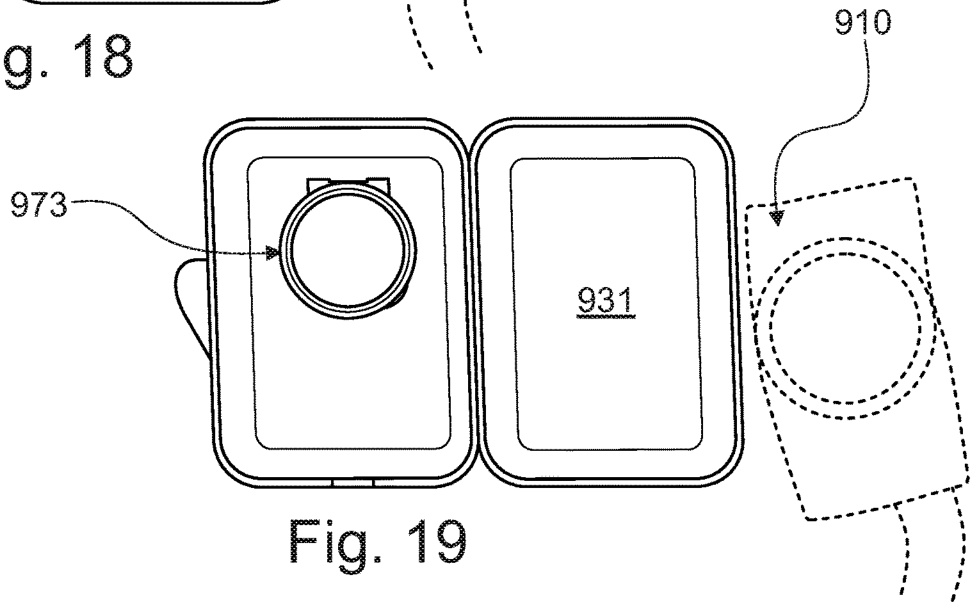
Figure 20:
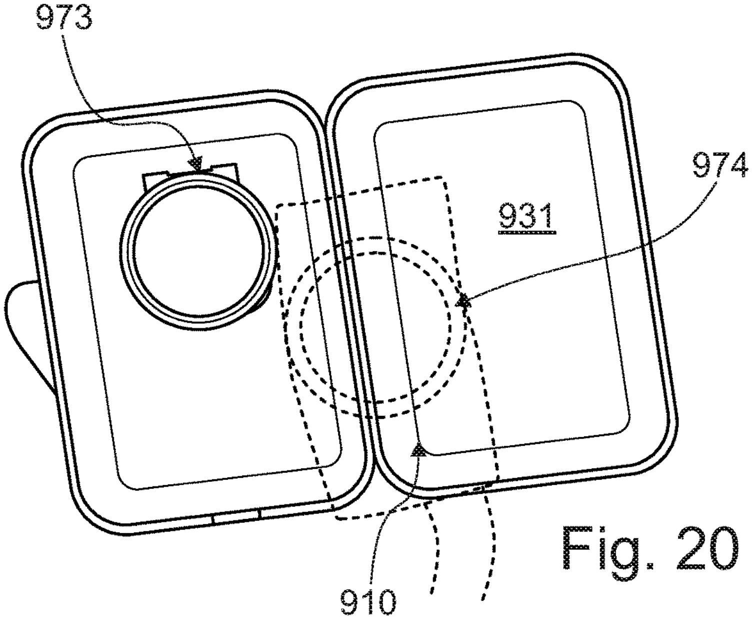

FIG. 15-17 illustrates holding means 800 for a box, the box is in the figure the same box 130 as in FIG. 1, however any type of box as disclosed herein may be used. The holding means 800 consists of two arms 801, 802, which are foldable between three configurations. A first configuration, where the arms are folded in under the box—this is mostly convenient for storage purposes (FIG. 13). In a second configuration, the arms are folded downwards, such that they can be used to grab around a thigh of a user (FIG. 14). In a third configuration, the arms are folded outwards such that they provide a larger base for positioning the box across both thighs of the user (FIG. 15). In the illustrated embodiment, the arms 801, 802 comprises hinges 803, 804 allowing for 180 degrees movement of them.

Figure 21:
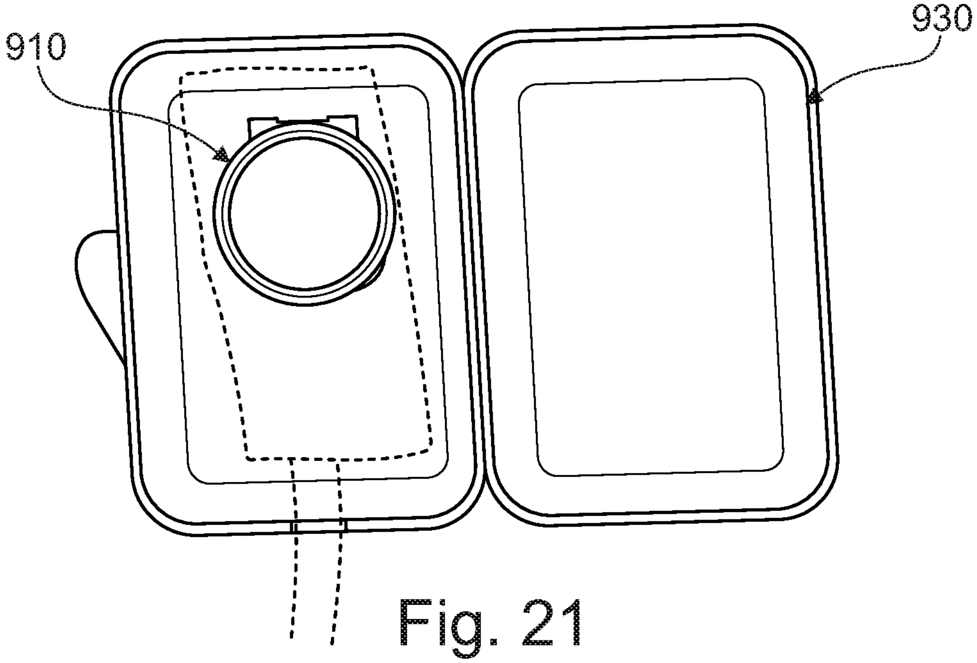
Figure 22:
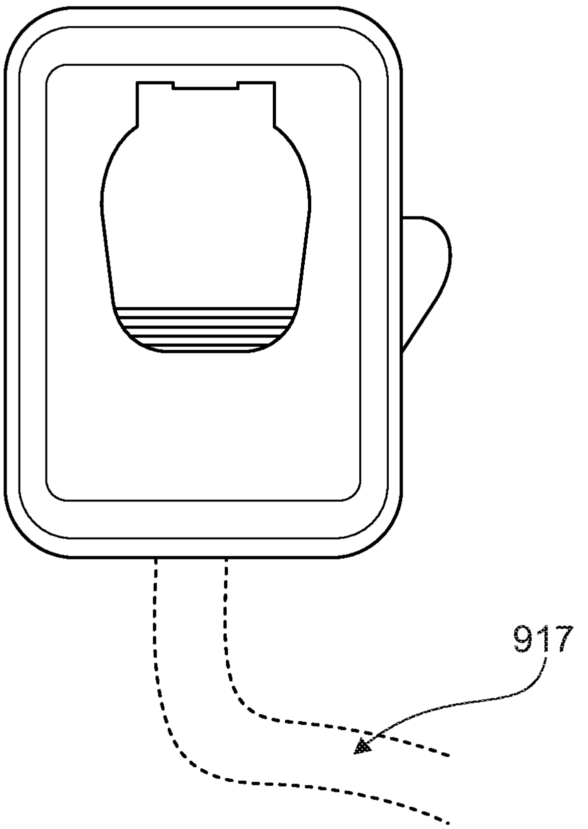
Figure 23:
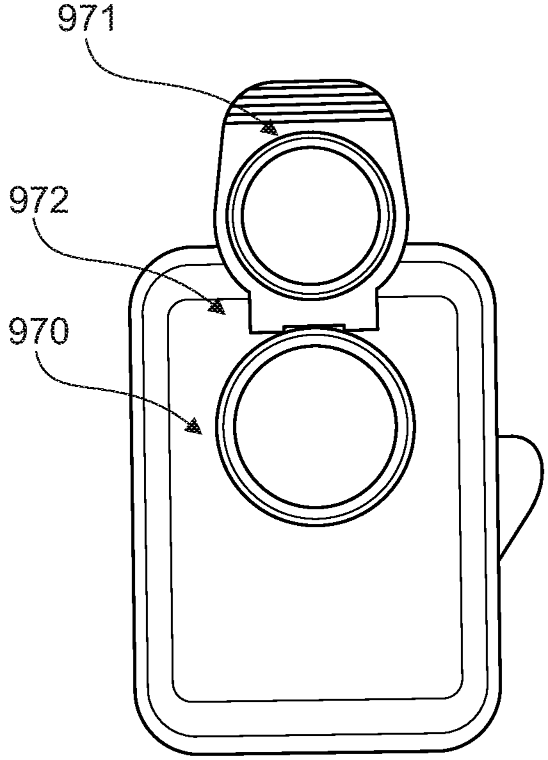
Figure 24:
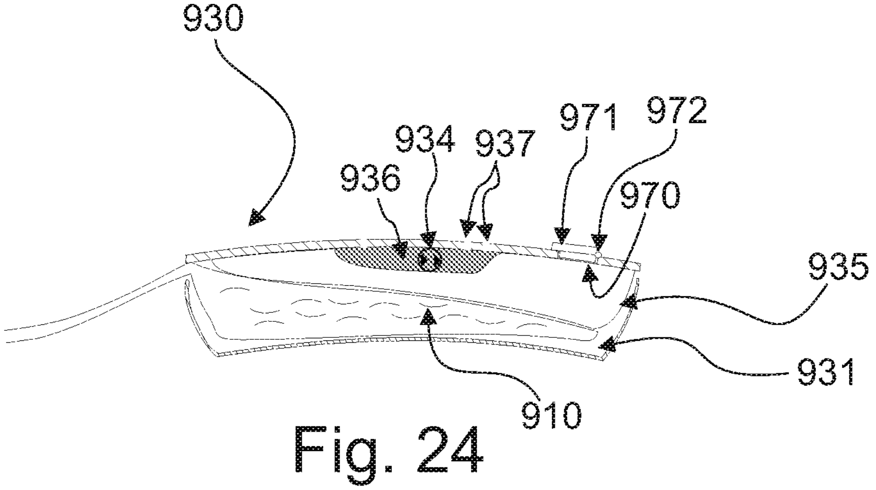
FIG. 24 illustrate a cross-sectional view of a box for use in anal irrigation system.

FIGS. 18 to 23 illustrate steps of preparing a box 930 and a reservoir 910 for use in a complete anal irrigation system. FIG. 24 illustrates a cross-sectional view of the same box 930 and 910 when it is ready to use. The tubes 917 can be seen in FIG. 21. The box has a cavity 931 which is configured for holding the reservoir 910 during use. The means for pressing may be in the form of a pump 934 and an inflatable lung 935 (see FIG. 24). As described in relation to FIG. 5, the pump 934 will be able to suck in air through the air-inlets 937. The pump 934 is positioned in a cavity 936 in the lid. The box has a filling opening 970, which can be closed by a closure 971. In the illustrated embodiment, the closure 971 is attached to the box 930 at hinge 972—however, the closure may be completely removable from the box. On the interior side of the filling opening 970, the box is provided with second coupling means 973 which is adapted for cooperating with first coupling means 974 on the reservoir bag 910. The first coupling means 974 can be seen in FIG. 20. In FIG. 21, the first and second coupling means are coupled together, such that the reservoir 910 is attached to the box 930 at the filling opening. In FIG. 22, the lid on the box is closed and the reservoir is now inside the cavity of the box. FIG. 23 illustrates how the closure 971 can be opened so as to allow filling of the reservoir inside the box through the filling opening 970.

Figure 25:
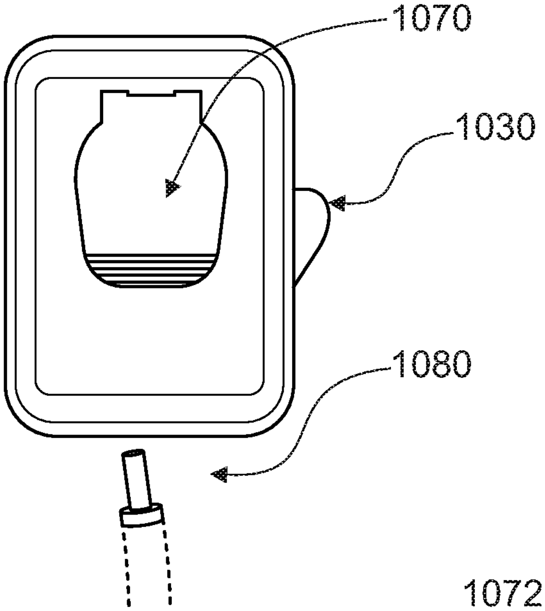
FIGS. 25-27 illustrate a box with an inflatable lung, which can be used without a reservoir.
Figure 26:
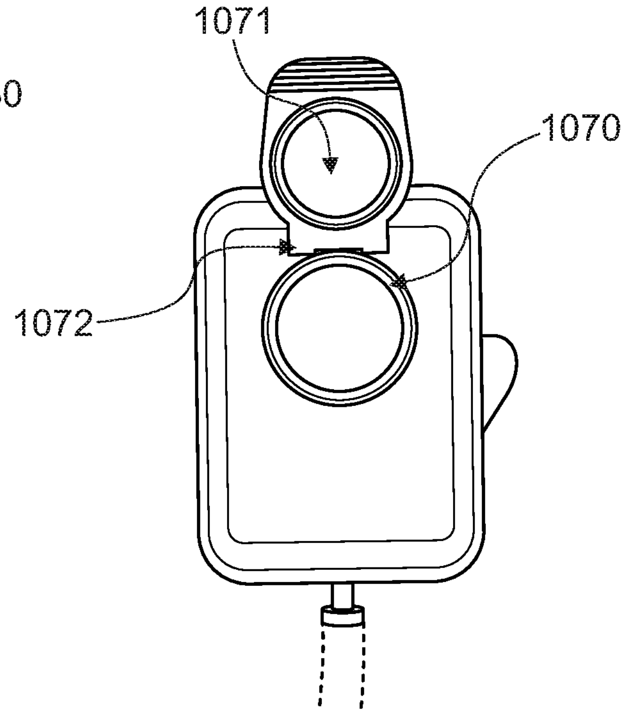
Figure 27:
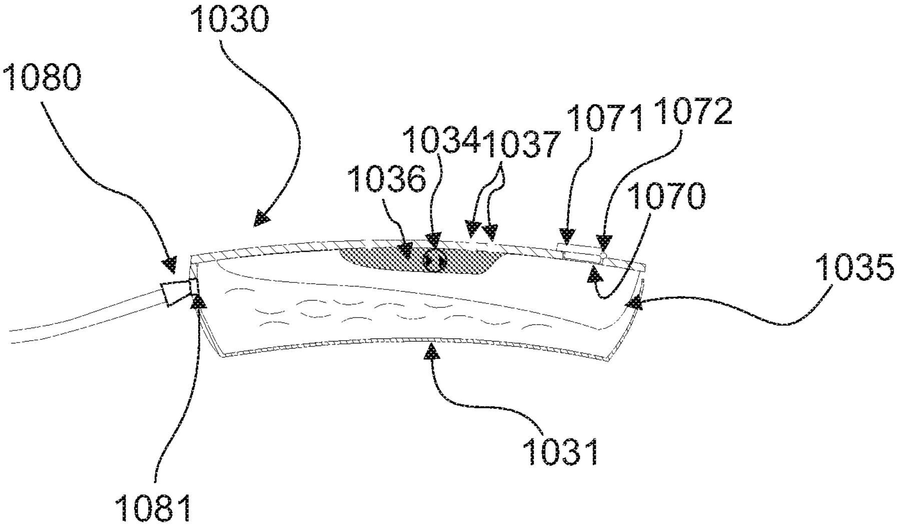

FIGS. 25-27 illustrate a box 1030 which can be used without a reservoir. The box is closed and provided with a filling opening 1070, which can be closed by a closure 1071. Like with the box 930 in FIGS. 18-24, this closure 1071 is attached to the box 1030 via a hinge 1072, however, the closure may be completely removable from the box. Liquid is filled into a cavity 1031 of the box through the filling opening 1070 and will flow around freely in this cavity 1031 (see FIG. 27). The means for pressing comprise a pump 1034 and an inflatable lung 1035, which functions as described above. The pump 1036 is positioned in a second cavity 1036 in the box 1030 and air is fed to the pump through air-inlets 1037 (see FIG. 27). The tubes 1017 are connected to the box by a luer-connector 1080 on the tube cooperating with a through-going opening 1081 on the box. Other types of connectors may be used, such as bayonet couplings or threaded connectors.

The invention claimed is:

1. An anal irrigation system comprising:

a reservoir having a first wall sealed to a second wall to form a container adapted to hold a volume of liquid;

a tube connected to the reservoir;

an anal probe connected to the tube;

a box comprising:

a floor, opposing lateral side walls attached to the floor, opposing end walls each attached to the floor and to the opposing lateral side walls, a tube opening formed in one of the opposing end walls, a first cavity inside of the box sized to receive the reservoir, a lid that moves to expose the first cavity, and a second cavity formed in the lid;

an inflatable lung the inflatable lung comprising:

a plurality of chambers, each of which is inflatable to pressurize to increase a size of the inflatable lung, wherein the inflatable lung is located within the first cavity; and a pump, the pump adapted to pump air into the inflatable lung, wherein the increase in size of the inflatable lung in turn applies pressure to the reservoir such that the reservoir is compressed to displace a portion of the volume of liquid through the tube and out of the anal probe, and wherein the pump is within the second cavity.

2. The anal irrigation system of claim 1, wherein the lid is hinged relative to the box.

3. The anal irrigation system of claim 1, wherein the anal probe is permanently fixed to the tube.

4. The anal irrigation system of claim 1, further comprising an attachment strap connected to the box, where the attachment strap is configured to secure the box to a leg of a user.

5. The anal irrigation system of claim 1, wherein the box further comprises a fill spout, and the fill spout is adapted to couple with the container to allow additional liquid to be added to the container.

6. The anal irrigation system of claim 1, wherein the reservoir further comprises an end wall sealed between the first wall and the second wall, and the tube is sealed to the end wall.

7. The anal irrigation system of claim 1, wherein the box is a rectangular box forming a rectangular first cavity and the reservoir is a rectangular reservoir that is sized to fit in the rectangular first cavity.

8. The anal irrigation system of claim 1, wherein the plurality of chambers provides feedback to a user indicating an amount of inflation of the inflatable lung and correlated to the portion of the volume of liquid displaced from the reservoir.

9. The anal irrigation system of claim 1, wherein the pump comprises air inlets allowing the pump to draw air into the pump for inflating the inflatable lung.

10. An anal irrigation system comprising:

a reservoir having a first wall sealed to a second wall to form a container adapted to hold a volume of liquid;

a tube connected to the reservoir;

an anal probe connected to the tube;

a box comprising:

a floor, opposing lateral side walls attached to the floor, opposing end walls each attached to the floor and to the opposing lateral side walls, a tube opening formed in one of the opposing end walls, a first cavity inside of the box sized to receive the reservoir, a lid, the lid comprising air inlets, wherein the lid moves to expose the first cavity; and an inflatable lung, the inflatable lung comprising:

a plurality of chambers, each of which is inflatable to a pressurize to increase a size of the inflatable lung, wherein the inflatable lung is located within the first cavity; and a pump, the pump adapted to pump air into the inflatable lung, wherein the increase in size of the inflatable lung in turn applies pressure to the reservoir such that the reservoir is compressed to displace a portion of the volume of liquid through the tube and out of the anal probe, and wherein the pump draws air into the box via the air inlets within the lid.

* * * * *